(12) United States Patent
Mohler et al.

(10) Patent No.: US 6,593,155 B2
(45) Date of Patent: Jul. 15, 2003

(54) METHOD FOR DETERMINATION OF CURE AND OXIDATION OF SPIN-ON DIELECTRIC POLYMERS

(75) Inventors: Carol E. Mohler, Midland, MI (US); Robert A. Devries, Midland, MI (US)

(73) Assignee: Dow Global Technologies Inc., Midland, MI (US)

( * ) Notice: Subject to any disclaimer, the term of this patent is extended or adjusted under 35 U.S.C. 154(b) by 0 days.

(21) Appl. No.: 09/751,484

(22) Filed: Dec. 28, 2000

(65) Prior Publication Data

US 2002/0086429 A1 Jul. 4, 2002

(51) Int. Cl.[7] ............................................. G01R 31/26
(52) U.S. Cl. ..................... 438/16; 438/780; 422/82.08; 430/270.15
(58) Field of Search .................................. 438/780, 783, 438/778, 16; 422/82.08; 430/270.15; 356/318

(56) References Cited

U.S. PATENT DOCUMENTS

| | | | |
|---|---|---|---|
| 4,717,674 A | 1/1988 | Sung | 436/85 |
| 4,885,254 A | 12/1989 | Sung | 436/85 |
| 5,100,802 A | 3/1992 | Mickols | 436/34 |
| 5,155,175 A | 10/1992 | Mercer et al. | 525/390 |
| 5,179,188 A | 1/1993 | Mercer et al. | 528/219 |
| 5,532,817 A | 7/1996 | DeVries et al. | 356/318 |
| 5,598,005 A | 1/1997 | Wang et al. | 250/459.1 |
| 5,707,587 A * | 1/1998 | Blanchard et al. | 422/82.08 |
| 5,874,516 A | 2/1999 | Burgoyne, Jr. et al. | 528/219 |
| 5,955,002 A | 9/1999 | Neckers et al. | 252/301.35 |
| 5,965,679 A | 10/1999 | Godschalx et al. | 526/281 |
| 6,342,454 B1 * | 1/2002 | Hawker et al. | 438/623 |
| 2002/0025490 A1 * | 2/2002 | Shchegolikhin et al. | 430/270.15 |

FOREIGN PATENT DOCUMENTS

| | | |
|---|---|---|
| EP | 0 720 015 A2 | 7/1996 |
| EP | 0 755 957 B1 | 5/1999 |
| WO | WO 86/07456 | 12/1986 |
| WO | WO 91/09081 | 6/1991 |
| WO | WO 97/01593 | 1/1997 |
| WO | WO 97/10193 | 3/1997 |

OTHER PUBLICATIONS

C. Burgess et al., "Spectrophotometry, Luminescence and Colour; Science & Compliance" 1995, Elvsevier, 1st ed. vol. 6, pp. 178–186, 192–193 and 259–262.*

Sun, et al., "Intrinsic Fluorescence Cure Sensor for Reaction Monitoring in Polyurethane," *Polymer Preprints,* vol. 35, No. 1, pp. 435–436, (Mar. 1994).

Grunden, et al., "Cure Monitoring of Styrene Containing Polymers Using UV–Reflection and Fluorescence Spectroscopies," *Polymer Preprints,* vol. 37, No. 1, pp. 477–478 (Mar. 1996).

N.H. Hendricks and K.S.Y Lau, *Polym. Prepr.* (Am. Chem. Soc., Div. Polym. Chm.) 1996, 37 (1), pp. 150–151.

*Material Res. Soc, Symp. Proc.* (1997), vol. 476 (Low Dielectric Constant Materials III), pp. 121–128.

(List continued on next page.)

Primary Examiner—William David Coleman

(57) ABSTRACT

This invention is a method comprising preparing a sample by coating a thin film of a precursor material, which is free of fluorescent probe molecules onto a substrate and subjecting the precursor material to conditions to attempt to cause cure of the precursor to an organic, aromatic, polymer having a dielectric constant of less than 3.0, exposing the sample to radiation having a wavelength in the range of 200 to 500 nm, detecting a resulting emission of radiation, and comparing the emission to the emission for a known cured, non-oxidized standard for the polymer.

13 Claims, 10 Drawing Sheets

OTHER PUBLICATIONS

Song, et al., "Cure Monitoring of UV Coatings Using a Fiber–Optic Fluorescence Technique," *Polymeric Materials Science and Engineering,* vol. 72, pp. 591–592 (1995).

"New Developments in Fluorescene Probe Technology for Cure Monitoring," *Radtech '98 North American UV/EB Conf.,* pp. 348–355.

Sung, et al., "UV and Emission Techniques for characterization of polymers and ocmposites," *Polymeric Materials Science and Engineering,* vol. 71, pp. 69–70 (1994).

*Radtech Report,* In Situ Cure Monitoring, vol. 12, pp. 27–32, 1998.

"Low–Dielectric Constant Materials–Synthesis and Applications in Microelectronics," *Materials Research Society Symposium Proceeding,* vol. 381, pp. 165–173 (1995).

"Monitoring of Curing of Polyurethane Polymers with Fluorescence Method," *Macromolecules,* vol. 33, pp. 438–443 (2000).

Aronow, et al., "In–Situ Cure Monitoring of Polyurethane/urea Cure with Fiberoptic Fluorescence Spectroscopy," *Polymer Preprints,* American Chemical Society, vol. 39, No. 2, pp. 642–643, (Aug. 1998).

Jager, et al., "Organic Donor–Acceptor Salts: A New Type of Probe for Monitoring Photopolymerization Processes," *Macromolecules,* vol. 29, pp. 7351–7355 (1996).

*Conference Proceedings,* "Monitoring Conventional and Microwave Curing of Polymers and Composites with the Fluorescence Optrode Cure Sensor (FOCS)," pp. 1668–1671 (1991).

Sun, et al., "Cure Characterization in Polyeurethane and Model Urethane Reactions by an Intrinsic Fluorescence Technique," *Macromolecules,* vol. 29, pp. 3198–3202 (1996).

Sung, et al., "Fluorescence characterization of cure and water uptake in polymers and composites," *Materials Science and Engineering, A162,* pp. 241–247(1993).

*Application of Fluorescence Spectroscopy in Polymer Science*: Quantaitiative Analysis of Cure, Diffusion, Phase Behavior, Sorption and Relaxation Behavior, p. 65.

Wang, et al. "Cure Monitoring of Bulk MDI–Based Polyure–Polyurethanes by In–Situ Emission Fluorescence," *Polymer Preprints,* vol. 37, No. 1, pp. 467–468 (Mar. 1996).

Woerdeman, et al. "Cure Monitoring in RTM Using Fluorescence," *Plastics Engineering,* Plastic Ayalysis, pp. 25–27 (1995).

Xu, et al., "Curve Characterization of Bisphenol A Dicyanate Ester by Fluorescence, UV and FTIR spectroscopy," *Polymer Preprints,* vol. 36, No. 2, pp. 356–357 (Aug. 1995).

Song, et al., "Monitoring Degree of Cure and Coating Thinckness of Photocurable Resins Using Fluorescence Probe Techniques," *American Chemical Society,* Chapter 28, pp. 473–487 (1995).

* cited by examiner

METHOD FOR DETERMINATION OF CURE AND OXIDATION OF SPIN-ON DIELECTRIC POLYMERS

FIELD OF THE INVENTION

This invention relates to a method for determining cure and/or detecting oxidation of spin-on dielectric polymers.

BACKGROUND OF THE INVENTION

The microelectronics fabrication industry is moving toward smaller geometries in its devices to enable lower power and faster speeds. As the conductor lines become finer and more closely packed, the requirements of the dielectrics between such conductors become more stringent. One class of materials being examined as a replacement for the standard dielectric material, silicon dioxide, is spin-on dielectric (SOD) polymers.

Unlike the traditional silicon dioxide dielectric layers, these dielectric layers are formed by applying a solution containing the oligomeric precursor to the dielectric polymer, spinning to evenly coat and to remove solvent, followed by curing of the polymer. Curing typically occurs by heating the coated substrate to initiate additional polymerization reaction and/or cross-linking. Achieving an adequate degree of cure is essential to minimizing change in mechanical or other properties later on during fabrication or even during use of a device having a SOD polymer. An undesirable oxidation reaction may also occur if cure conditions (such as exposure to oxygen or other oxidants) are not adequately controlled. Detection of such oxidation reactions may also be important to assuring quality control.

Fluorescence has been taught to measure cure, potentially in-situ, of various polymers with the addition of a fluorescent probe (see, e.g., U.S. Pat. No. 5,100,802 and WO86/07456). However, the addition of a probe molecule would be undesirable due to the need for purity and due to high processing temperatures in the microelectronics fabrication process. Intrinsic fluorescence has also been taught as a method for monitoring cure in polyurethanes, (see, e.g., Sun, et al., "Intrinsic Fluorescence Cure Sensor for Reaction Monitoring in Polyurethane," *Polymer Preprints*, Vol. 35, No. 1, page 435, March 1994, and in polyester/styrene polymers (see, e.g., Grunden, et al., "Cure Monitoring of Styrene Containing Polymer Using UV-Reflection and Fluorescence Spectroscopies," *Polymer Preprints*, Vol. 37, No. 1, March, 1996). However, it was unknown whether SOD polymers possessed this characteristic.

Various analysis methods have been examined to determine cure and oxidation of SOD polymers. FT-Raman analysis can be used to monitor cure of extent of cure, but this method is destructive to the sample. Refractive index may also provide some indication of cure, but it is not very sensitive to oxidation. FT-IR analysis can be used to detect oxidation but is ineffective at detecting cure of important SOD polymers.

Therefore, a need remains for an efficient and cost-effective manner for detecting extent of cure and/or oxidation for spin-on dielectrics.

SUMMARY OF THE INVENTION

The Applicants have discovered a method that not only enables monitoring on-line of SOD for extent of cure but would also allow for simultaneous examination for oxidation. Thus, this invention is a method comprising preparing a sample by coating a thin film of a precursor material, which is free of fluorescent probe molecules onto a substrate and subjecting the precursor material to conditions to attempt to cause cure of the precursor to an organic, aromatic, polymer having a dielectric constant of less than 3.0, exposing the sample to radiation having a wavelength in the range of 200 to 500 nm, detecting a resulting emission of radiation, and comparing the emission to the emission for a known cured, non-oxidized standard for the polymer.

DETAILED DESCRIPTION OF THE INVENTION

Figure 1:
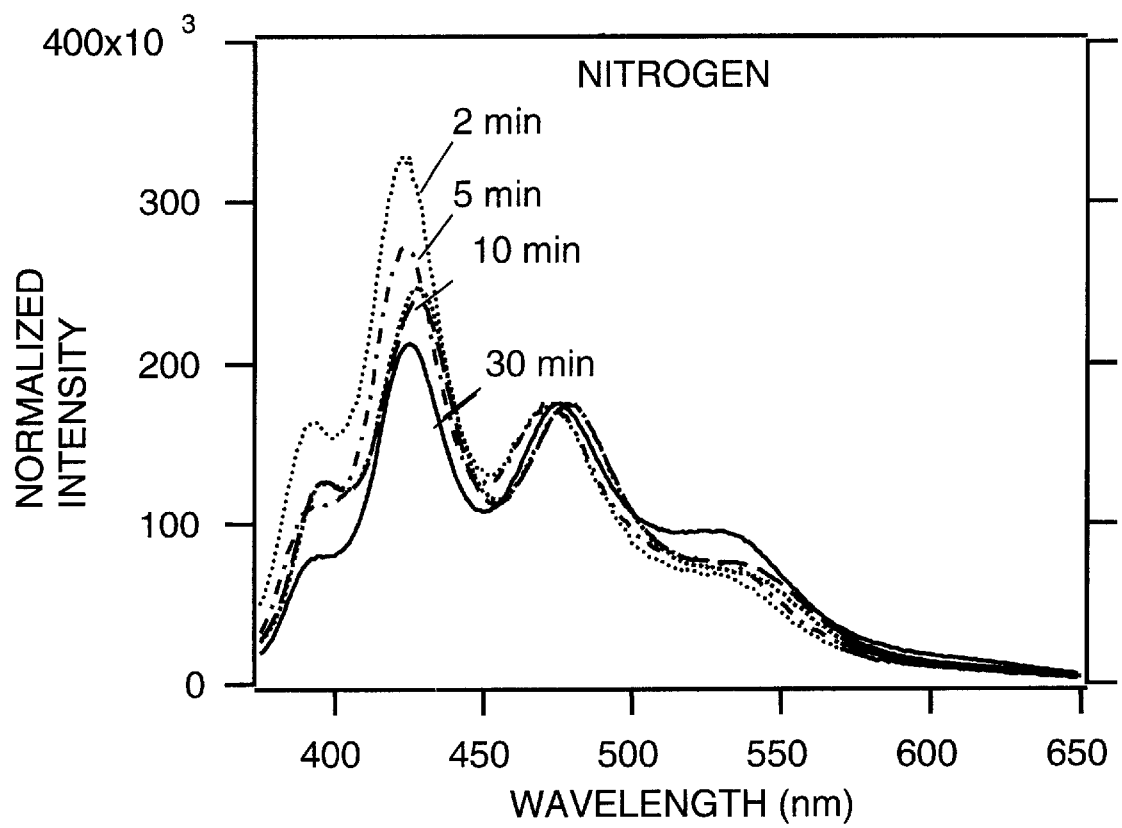
FIG. 1 is a graph of the fluorescence emission spectra (emission intensity versus emission wavelength) of the polymeric reaction product of a cyclopentadienone functional compound and an aromatic acetylene functional compound cured in a nitrogen atmosphere.

Generally, fluorescence behavior can be tested in two manners. First, in an excitation scan method, the wavelength of radiation applied to a sample is varied over a range of wavelengths and the sample is observed for emissions of radiation at one or more set wavelengths. This method maps the excited state for a fluorescent molecule, i.e., the excitation spectrum. However, preferably, an emission spectrum is obtained. In this second method, the wavelength of the radiation applied to a sample is held at a fixed value and the wavelengths of emission are collected over a range of wavelengths. This method maps the energy level for the ground state.

After obtaining the excitation or emission spectrum for the sample, that spectrum is compared to a spectrum for a sample having a known degree of cure and a known degree of oxidation. This comparison may reveal cure and/or oxidation in at least one of three manners—change in band wavelength position, change in band width, or change in band or peak intensity.

For the first two approaches, there is a shift in the wavelength where peak intensity occurs and/or a broadening of the peak or band. Alternatively, or in addition, the intensity of the emission at a given wavelength may have changed. A potential drawback of the latter method is that due to the inherent variability in determining absolute fluorescence intensities, the comparison of the test sample to the standard will need to be comparison of a normalized value for the test sample to a normalized value for the sample.

Thus, according to one preferred embodiment, a sample is exposed to radiation having an effective excitation wavelength, and the emission intensity is measured for at least three predetermined wavelengths. The first predetermined wavelength, referred to herein as the cure responsive wavelength, corresponds to a wavelength at which emission intensity is known to vary with cure. The second predetermined wavelength, referred to as the oxidation responsive wavelength, corresponds to a wavelength at which emission intensity is known to vary with oxidation. The third predetermined wavelength, referred to as the non-responsive wavelength, corresponds to a wavelength, which remains relatively unchanged with cure and oxidation reactions. The raw values for intensity at each of the cure responsive and oxidation responsive wavelengths are normalized by dividing the raw values of intensity for each by the value for intensity at the non-responsive wavelength to yield a cure intensity ratio and an oxidation intensity ratio. These ratios can then be compared to the cure intensity ratio and oxidation intensity ratio for at least one standard having a known degree of cure and oxidation. Thus, the degree of cure and oxidation can be estimated based on the difference in these ratios between the test sample and the standard. Use of more than one standard having different known degrees of cure and oxidation will provide more precise information about the degree of cure and oxidation.

According to a second embodiment, the first preferred embodiment is used except, rather than plotting emission wavelength versus intensity, the emission (detection) wavelength is held constant and the excitation wavelength is varied. Intensity of emission is then plotted against excitation wavelength and a similar normalization procedure as set forth in the first embodiment is used.

According to a third preferred embodiment, the detection wavelength is held constant but the excitation wavelength is varied and the intensity of emission at the detection wavelength for the various excitation wavelengths is determined. The excitation wavelength, which causes the maximum (i.e., peak) emission intensity, is determined and is compared to the excitation wavelength, which causes the peak emission intensity for at least one standard having a known degree of cure and oxidation. The difference in peak wavelength will indicate how close the sample is to the degree of cure and oxidation in the standard. This method avoids the necessity of normalization, but suffers from the fact that the effect of cure reaction on peak shift could be negated or enhanced by the effect of the oxidation reaction on peak shift, thereby yielding confusing results. In fact, unless there is more than one peak that can be analyzed, this method is less accurate in providing simultaneous cure and oxidation information. There is an analogous fourth method, which bases the determination of degree of cure and oxidation on peak shift but holds excitation wavelength constant and plots intensity of emission versus emission wavelength. This method suffers from the same drawback that, unless there is more than one peak, the separate effects of cure and oxidation may be difficult to determine.

According to a fifth embodiment, a sample is exposed to radiation having an effective excitation wavelength, the emission spectra is obtained. Band width of a select peak or band is measured at half the band height and compared to that for a standard having a known degree of cure and oxidation. The difference in band width will indicate how close the sample is to the known degree of cure and oxidation. There is an analogous method, which base varies the excitation wavelength and measures emission at a set wavelength. The plot obtained is a plot of emission intensity versus excitation wavelength. A similar band width measurement can be made and compared to band width for a standard.

Which methods (excitation scan vs. emission scan and peak shift, width or intensity) are more appropriate may depend upon the characteristics of a specific SOD.

Applicants believe the method of this invention would be useful in simultaneously detecting cure and oxidation of various aromatic SOD polymers. Preferably, the SOD polymer is an organic polymer having no, or substantially no, Si atoms in the backbone. Polyarylenes are especially preferred. Examples of polyarylenes include the poly(arylene ethers) (i.e., PAE resins—Air Products) that are described in EP 0 755 957 B1, Jun. 5, 1999 and/or the FLARE resins made by Allied Signal Corp. (see N. H. Hedricks and K. S. Y Liu, *Polym. Prepr.* (Am. Chem. Soc., Div. Polym. Chm.) 1996, 37(1), pages 150–1; also J. S. Drage, et al., *Material Res. Soc, Symp. Proc.* (1997), Volume 476 (Low Dielectric Constant Materials III), pages 121–128 and those described in U.S. Pat. Nos. 5,115,082; 5,155,175; 5,179,188 and 5,874,516 and in PCT WO91/09081; WO97/01593 and EP 0755957-81. Alternatively, the polyarylene may be as disclosed in WO97/10193. Preferably, however, the polyarylene is the reaction product of a cyclopentadienone functional compound and an aromatic acetylene functional compound, as disclosed in those disclosed in U.S. Pat. No. 5,965,679, incorporated herein by reference. Fluorescence analysis for simultaneous detection of cure and oxidation for these latter preferred polyarylenes works particularly well as these polymers display peaks at distinct wavelengths for oxidation and cure, respectively.

The precursors (i.e., curable oligomer or polymer) are preferably of the general formula:

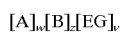

wherein A has the structure:

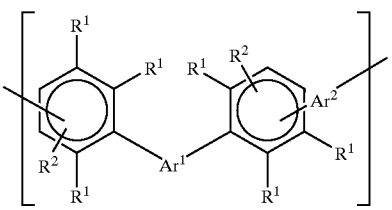

and B has the structure:

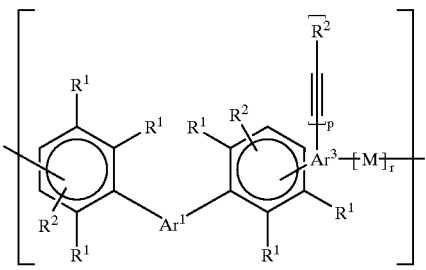

wherein EG are end groups having one or more of the structures:

EG =

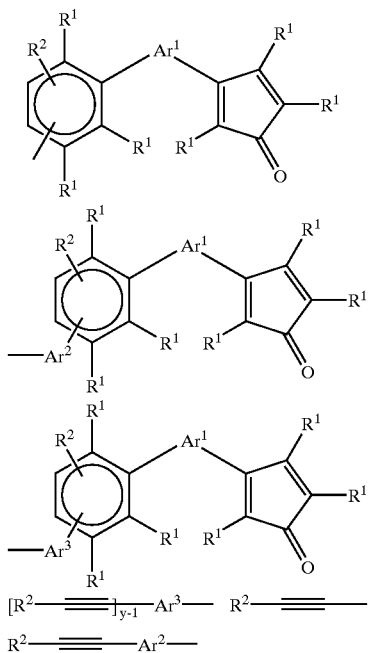

wherein $R^1$ and $R^2$ are independently H or an unsubstituted or inertly-substituted aromatic moiety and $Ar^1$, $Ar^2$ and $Ar^3$ are independently an unsubstituted aromatic moiety or inertly-substituted aromatic moiety, M is a bond, and y is an integer of three or more, p is the number of unreacted acetylene groups in the given mer unit, r is one less than the number of reacted acetylene groups in the given mer unit and p+r=y−1, z is an integer from 0 to about 1000; w is an integer from 0 to about 1000 and v is an integer of two or more.

Such oligomers and polymers can be prepared by reacting a biscyclopentadienone, an aromatic acetylene containing three or more acetylene moieties and, optionally, a polyfunctional compound containing two aromatic acetylene moieties. Such a reaction may be represented by the reaction of compounds of the formulas (a) a biscyclopentadienone of the formula:

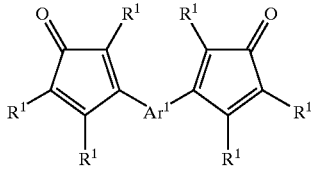

(b) a polyfunctional acetylene of the formula:

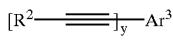

(c) and, optionally, a diacetylene of the formula:

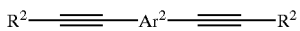

wherein $R^1$, $R^2$, $Ar^1$, $Ar^2$, $Ar^3$ and y are as previously defined.

The definition of aromatic moiety includes phenyl, polyaromatic and fused aromatic moieties. Inertly-substituted means the substituent groups are essentially inert to the cyclopentadienone and acetylene polymerization reactions and do not readily react under the conditions of use of the cured polymer in microelectronic devices with environmental species, such as water. Such substituent groups include, for example, F, Cl, Br, —$CF_3$, —$OCH_3$, —$OCF_3$, —O—Ph and alkyl of from one to eight carbon atoms, cycloalkyl of from three to about eight carbon atoms. For example, the moieties, which can be unsubstituted or inertly-substituted aromatic moieties, include:

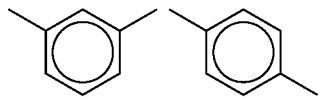

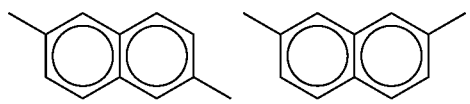

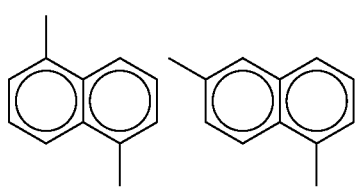

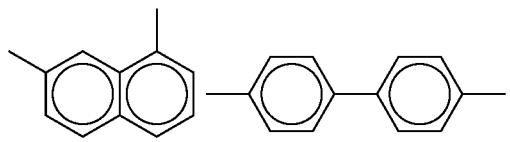

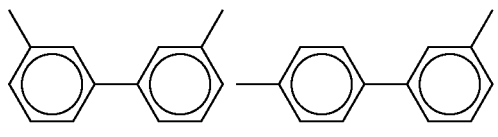

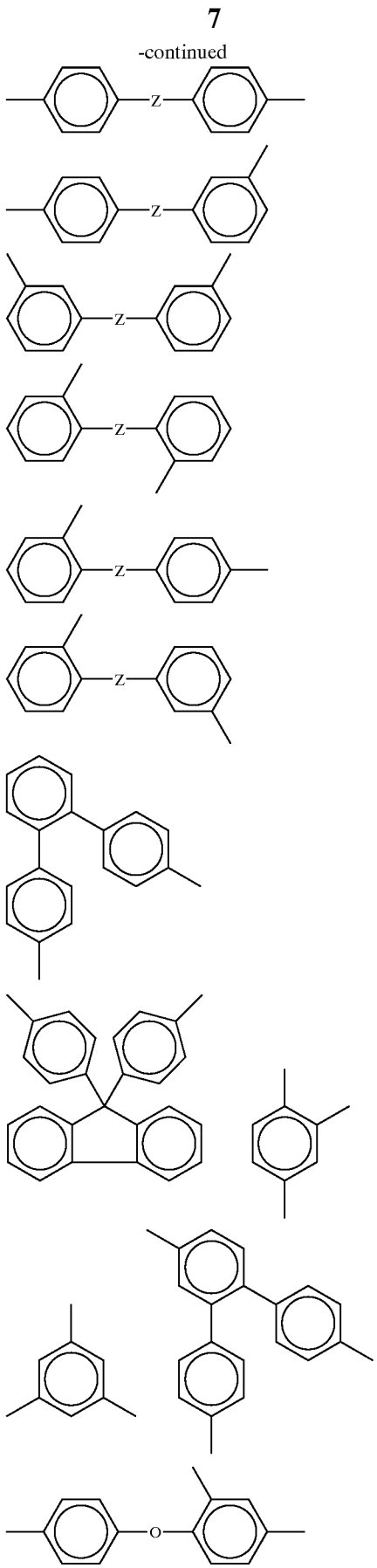

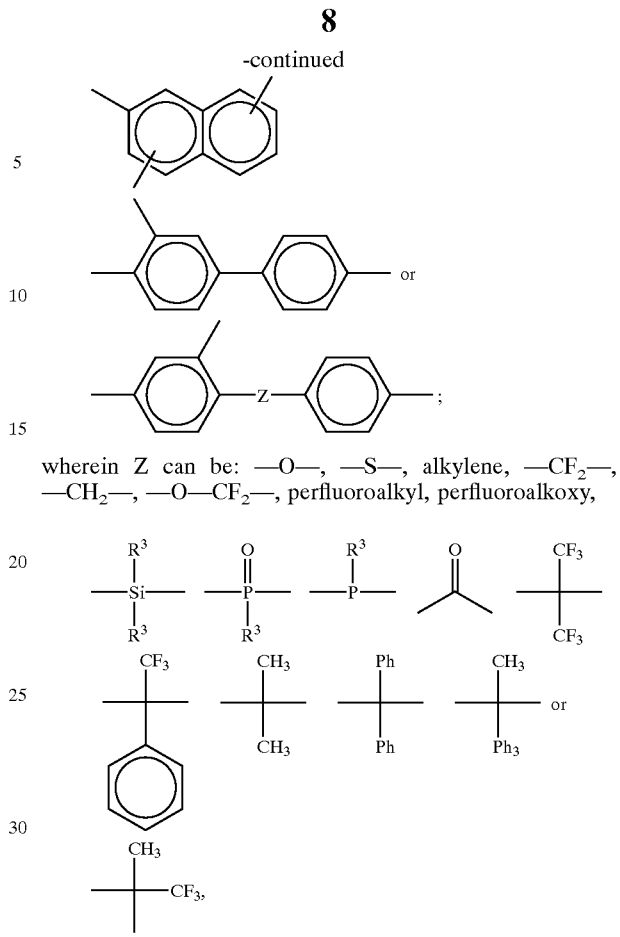

wherein Z can be: —O—, —S—, alkylene, —CF$_2$—, —CH$_2$—, —O—CF$_2$—, perfluoroalkyl, perfluoroalkoxy,

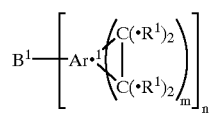

wherein each R$^3$ is independently —H, —CH$_3$, —CH$_2$CH$_3$, —(CH$_2$)$_2$CH$_3$ or Ph. Ph is phenyl.

For these preferred SODs, i.e., the reaction product of cyclopentadienone functional compound and aromatic acetylene compounds—an emission spectrum is preferably attained after applying radiation having a wavelength in the preferred range of 300 to 450 nm, more preferably 300 to 400 nm, and most preferably 330 to 390 nm. The cure responsive emission wavelength is in the range of about 380 to 440 nm, preferably in the range of 390 to 400 nm and/or 420 to 430 nm. The oxidation responsive wavelength is in the range of 500 to 650 nm, preferably 520 to 550 nm. The non-responsive wavelength is preferably in the range of 460 to 500 nm, more preferably 470 to 480 nm. To ensure a substantial degree of cure, the cure intensity ratio at wavelengths in the range 390 to 400 nm is preferably less than about 0.5 or in the range 420 to 430 nm less than about 1.4. The oxidation intensity ratio is preferably less than about 0.5 for oxidation responsive wavelengths in the range of 520 to 550 nm.

The methods outlined may also be applicable to BCB based polymers, which are the reaction product of monomers comprising (a) a cyclobutarene monomer having the formula:

$$B^1 \left[ Ar \cdot \left( \begin{matrix} C(\cdot R^1)_2 \\ C(\cdot R^1)_2 \end{matrix} \right)_m \right]_n$$

wherein
  B$^1$ is a n-valent organic linking group, preferably comprising ethylenic unsaturation, Ar¹ is a polyvalent aromatic or heteroaromatic group and the carbon atoms of the cyclobutane ring are bonded to adjacent carbon atoms on the same aromatic ring of Ar¹;

m is an integer of 1 or more;

n is an integer of 1 or more; and

R¹ is a monovalent group. The preferred BCB based polymers are the reaction product of the monomer (a) and has the formula

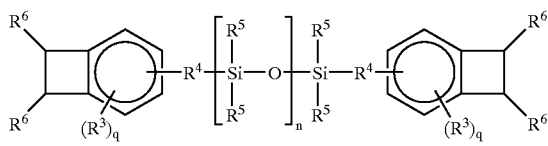

wherein each $R^3$ is independently an alkyl group of 1–6 carbon atoms, trimethylsilyl, methoxy or chloro; preferably $R^3$ is hydrogen;

each $R^4$ is independently a divalent, ethylenically unsaturated organic group, preferably an alkenyl of 1 to 6 carbons, most preferably —$CH_2$=$CH_2$—;

each $R^5$ is independently hydrogen, an alkyl group of 1 to 6 carbon atoms, cycloalkyl, aralkyl or phenyl; preferably $R^5$ is methyl;

each $R^6$ is independently hydrogen, alkyl of 1 to 6 carbon atoms, chloro or cyano, preferably hydrogen;

n is an integer of 1 or more; and each q is an integer of 0 to 3, some of which are commercially available under the trade name CYCLOTENE from The Dow Chemical Company.

BCB based polymers show an excitation wavelength peak shift to lower wavelengths with cure or an emission wavelength peak shift to higher wavelengths with cure. If oxidation is also occurring, the shift in peak emission wavelength to higher wavelengths is much larger. The width of the emission and excitation bands can also be used to detect oxidation since the width of these bands becomes much broader with oxidation.

The fluorescence spectrum of SOD films can advantageously be obtained by using flexible fiber optic probes attached to the fluorimeter. The center of the fiber optic bundle carries the excitation light to the sample, while the emitted light is returned to the emission monochromator of the fluorimeter via an outer ring of bundled fibers. This arrangement is advantageous since (1) it provides a very small area of the sample to be probed for cure and oxidation, (2) it allows the remote measurement of cure and oxidation, and (3) it allows for easy incorporation of the fluoresence emission technique to be automated into a tool capable of mapping the cure and oxidation across a sample. Spatial resolution of cure and oxidation can provide valuable feedback on curing tools (hot plates, vertical tube furnaces), in order to determine their temperature uniformity, as well as the quality of the nitrogen purge environment, in addition to ensuring uniformity in physical properties to improve device yield and performance. The feedback could also be used to increase cure time and/or temperature if the emission indicates incomplete cure.

EXAMPLES

Example 1

Fluorescence Emission Measurements of the Reaction Product of A Biscyclopentadienone Compound and A Trifunctional Aromatic Acetylene An oligomer solution made by the reaction of 3,3'-(oxydi-1,4-phenylene)bis(2,4,5-triphenylcyclopentadienone) and 1,3,5-tris(phenylethynyl)benzene in gamma-butyrolactone was later diluted with cyclohexanone and was spin coated on silicon substrates. The coated wafers were baked for 90 seconds at 320° C. on a nitrogen blanketed hot plate to remove residual solvent, and then placed on a nitrogen blanketed hot plate at 400° C., for 2, 5, 10, 20 and 30 minutes. Fluorescence emission spectra, as shown in FIG. 1, were collected on the samples using a Spex Fluorolog fluorimeter with front-face reflection optics, with excitation at 355 nm. The fluorescence spectra were normalized by the intensity of the band near 475 nm.

Figure 2:
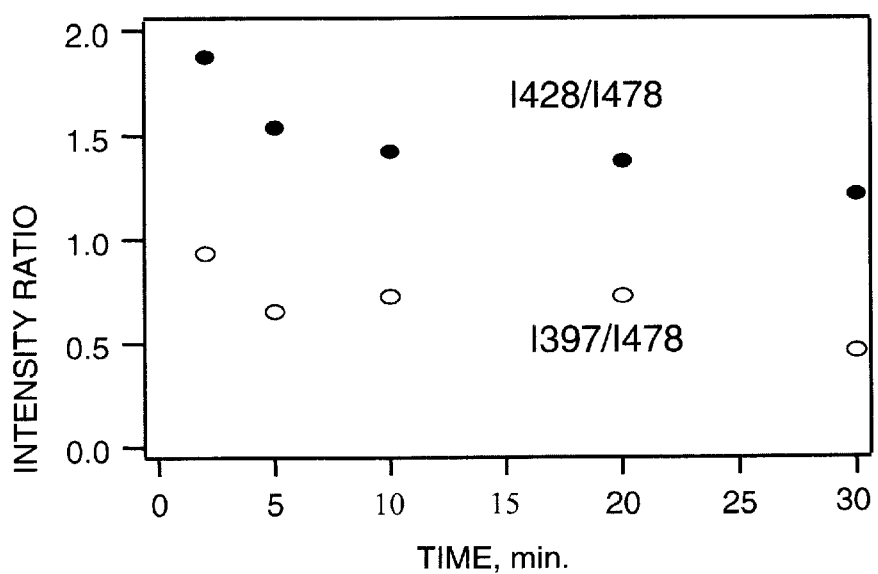
FIG. 2 is a graph of the normalized ratios of emission intensity at two emission wavelengths versus time of cure for the polymeric reaction product of a cyclopentadienone functional compound and an aromatic acetylene functional compound cured in a nitrogen atmosphere.

The normalized fluorescence spectra showed two bands that changed with cure time—one at 397, the other at 428 nm. As shown in FIG. 2, the plot of the normalized ratios I428/I475 and I397/I475 showed a decrease with cure time from 2 to 30 minutes, with a larger percentage change in the I397/I475 ratio. Either band or both bands can be used to quantitate cure.

Example 2

Fluorescence Emission Spectra of Oxidation

Figure 3:
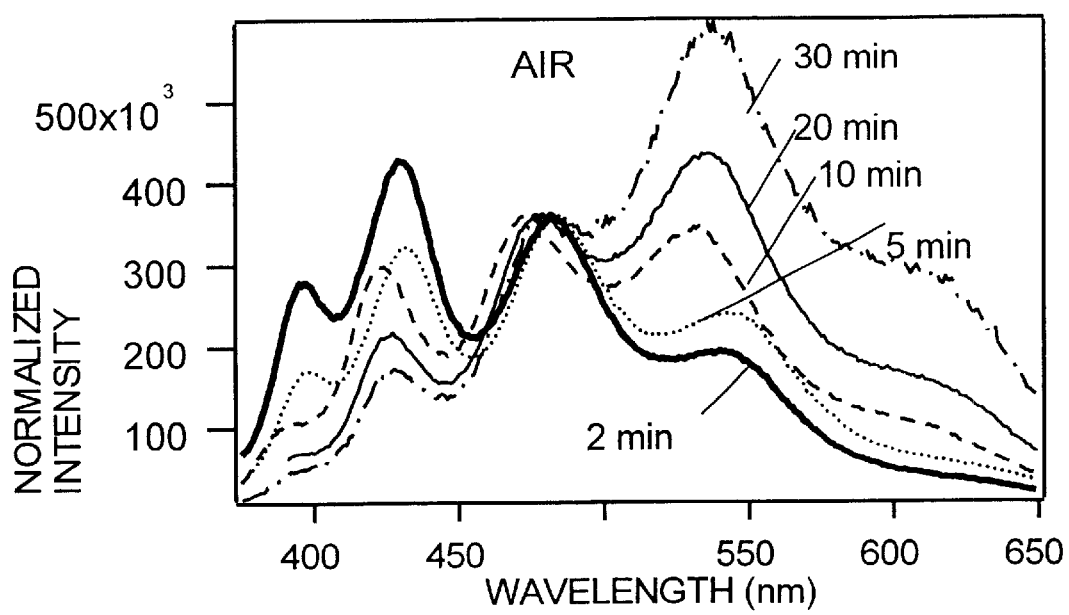
FIG. 3. is a graph of the fluorescence emission spectra of the polymeric reaction product of a cyclopentadienone functional compound and an aromatic acetylene functional compound cured in air.
Figure 4:
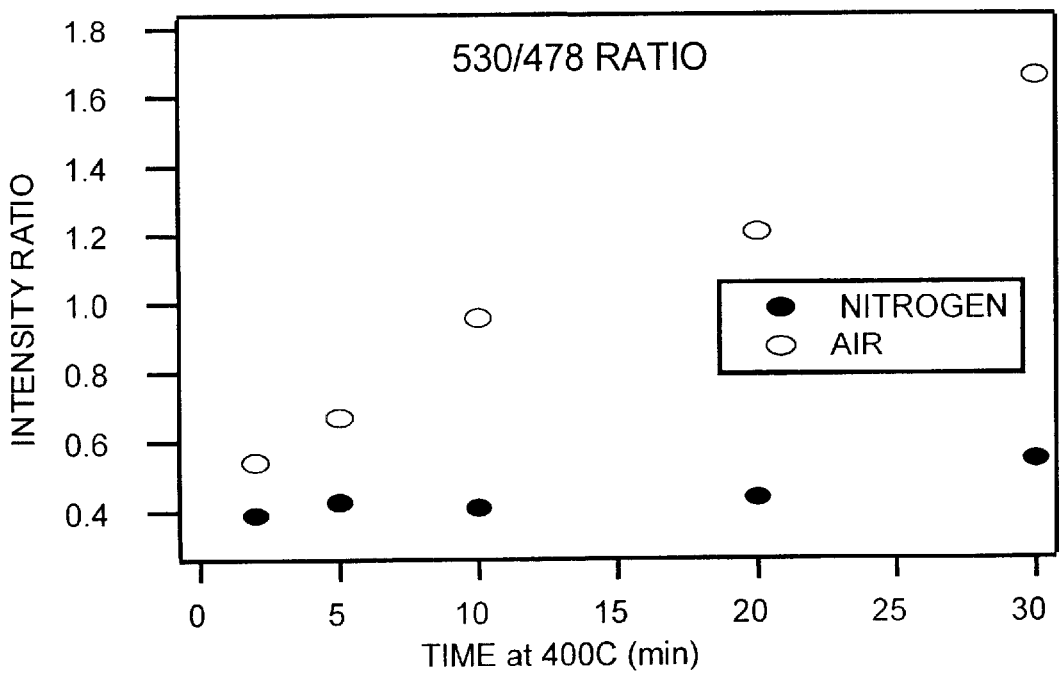
FIGS. 4–6 are graphs of the normalized emission intensity at three wavelengths for cures occurring in air and nitrogen versus time for the polymeric reaction product of a cyclopentadienone functional compound and an aromatic acetylene functional compound.
Figure 5:
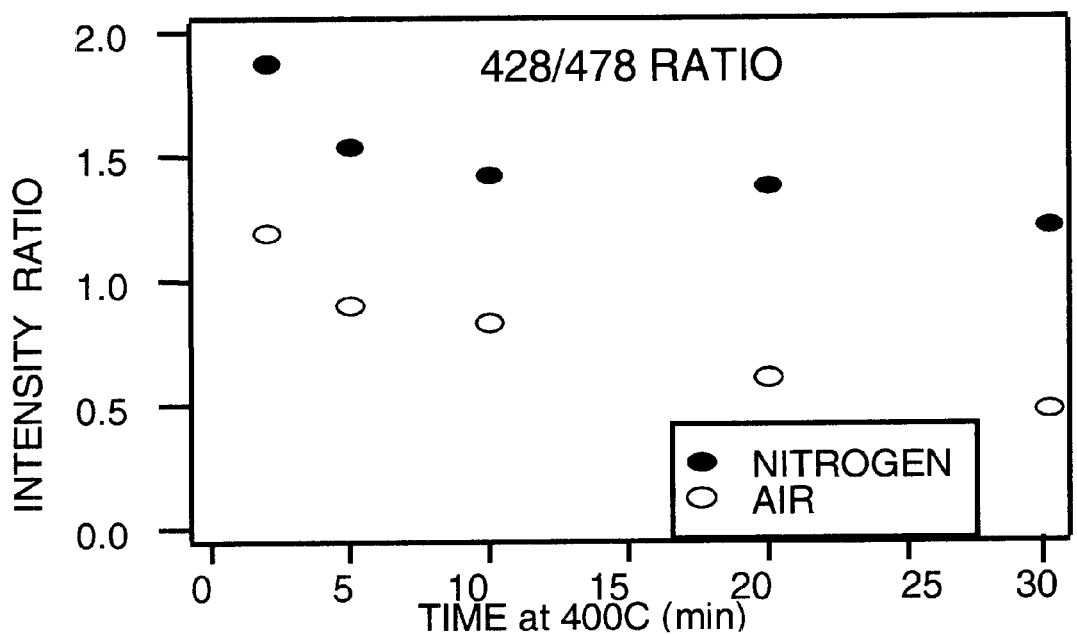
Figure 6:
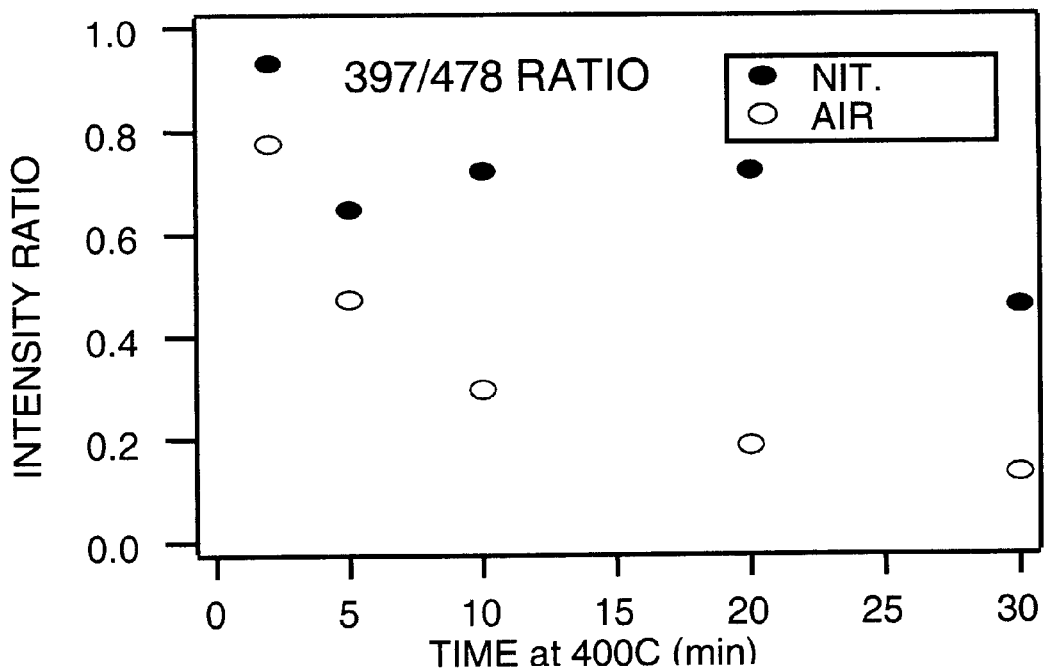

Films were prepared as in Example 1, except that the 400° C. hot plate cures were done in air, not under nitrogen. The fluorescence spectra were collected as in Example 1, and were likewise normalized by the intensity of the 475 nm band. As shown in FIG. 3, the normalized fluorescence spectra of films cured in air showed a large increase with cure time in the intensity of a band near 530 nm and a lesser increase in a shoulder near 630 nm. The bands at 428 and 397 nm also grew in intensity with cure time, as noted in example 1, because the polymer was curing, to some extent, even in the presence of oxygen. As shown in FIG. 4, the intensity ratio I530/I478 was relatively independent of cure time for films cured in nitrogen, but showed a sharp increase for films cured in air. As shown in FIGS. 5 and 6, the ratios I428/I478 and I397/I478 also showed a decrease with cure time in both air and nitrogen, but the decrease was much larger for cures in air than in nitrogen. Thus, the oxidation can be quantified by measuring the normalized ratio I530/I478, or by the ratios I428/I478 or I397/I478.

Figure 7:
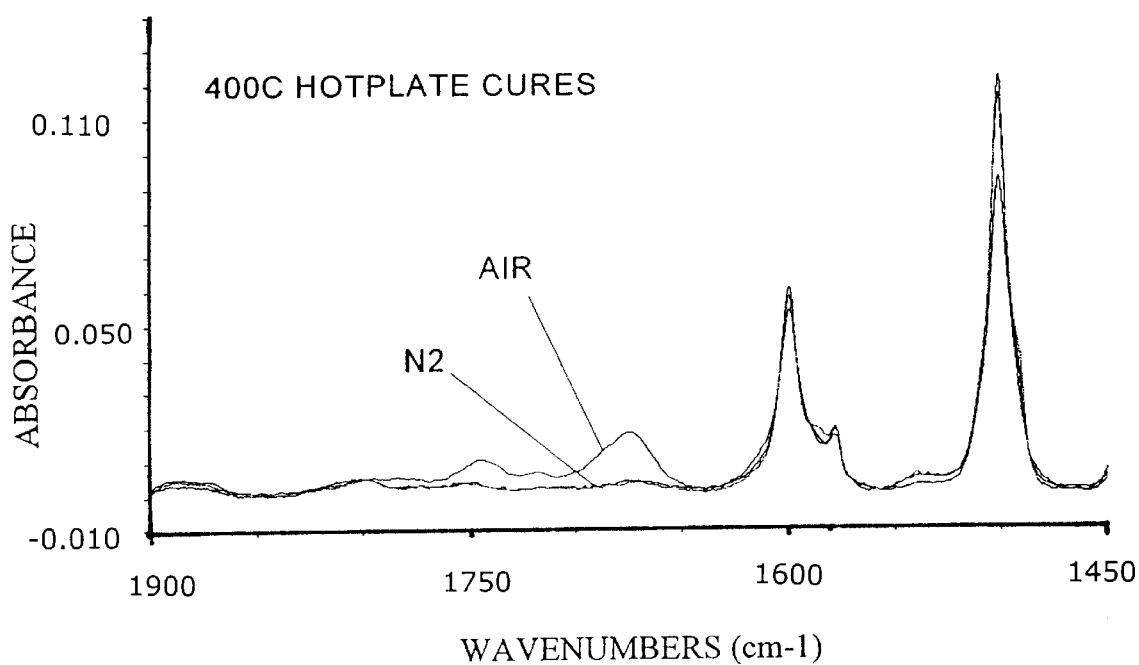
FIGS. 7 and 8 are FT-IR spectra for samples of the polymeric reaction product of a cyclopentadienone functional compound and an aromatic acetylene functional compound cured in air and nitrogen atmospheres.
Figure 8:
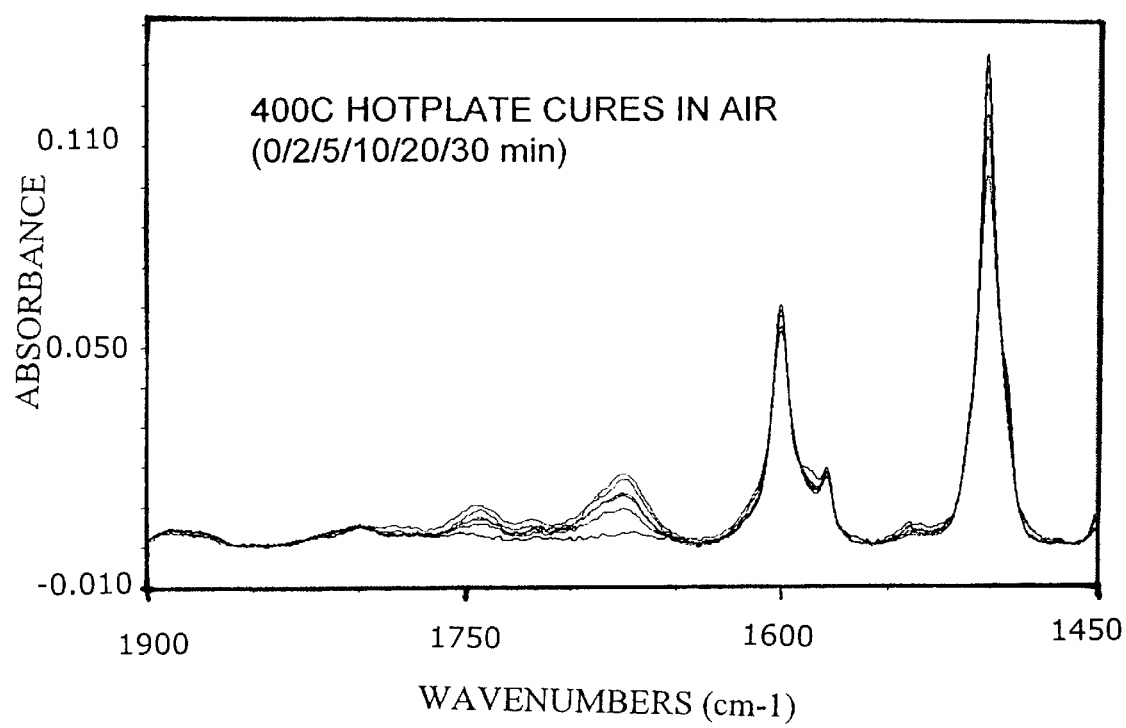

Verification that the changes in the fluorescence spectra were due to oxidation and not some other degradative process is given by the FT-IR spectra of the films. Transmission FT-IR spectra of the films cured in air and nitrogen were collected using a Nicolet Model 800 FT-IR spectrometer. As shown in FIGS. 7 and 8, the bands in the infrared spectrum near 1675 and 1740 cm-1, which grow in intensity during the cure in air (but not in nitrogen), were assigned to carbonyl groups, which were formed during the oxidation of the polymer. While the oxidation of the films could be monitored quantitatively by the growth of the 1675 cm-1 band in the FT-IR spectrum, the changes in the fluorescence emission spectrum were more sensitive in detecting oxidation than were FT-IR. The change in absorbance at 1675 cm-1 for a film oxidized at 400° C. for 30 minutes was approximately 0.005 absorbance unit for a 0.3 micron thick film. This was detectable by modem FT-IR spectrometers, but required significant signal averaging to detect a small increase in the baseline at 1675 cm-1 over the noise background. Alternatively, the same film oxidized at 400° C. for 30 minutes showed an increase in normalized fluorescence intensity at 530 nm by almost a factor of three (192,400 to 596,690), which was easily detectable, with little additional signal averaging.

Thus, the fluorescence emission spectrum of the films showed distinctive changes, which could be used to monitor both the cure and oxidation of the polymer. The changes in the spectrum due to cure were primarily found in the bands at 428 and 397 nm, while the oxidation of the polymer produced changes primarily at 530 nm. These regions of the fluorescence emission spectrum were sufficiently separated in wavelength that measurement of both the extent of cure and the detection and quanitification of oxidation could be accomplished in the same experimental measurement. This combination of cure and oxidation analysis is an advantage in time and money over conventional techniques, which require two separate methods for cure and oxidation (for example, RI for cure and FT-IR for oxidation).

Example 3

Fluorescence Measurements of CYCLOTENE BCB Based Resin Cure

The degree of cure of CYCLOTENE films can be monitored by either the excitation or emission spectra. Excitation spectra were collected for CYCLOTENE 3022 films prepared by spin-coating CYCLOTENE 3022-63 formulation on silicon substrates. The coated wafers were placed in a $N_2$-purged convection oven, and three different cure schedules were run to achieve different cure levels of the CYCLOTENE film. The cure schedules used were 150° C. for 30 minutes (to remove solvent), 210° C. for 30 minutes (soft cure) and 250° C. for 60 minutes (standard hard cure). Fluorescence excitation spectra were collected on the samples using a Spex Fluorolog fluorimeter with front-face reflection optics, with the emission collected at 370 nm.

Figure 9:
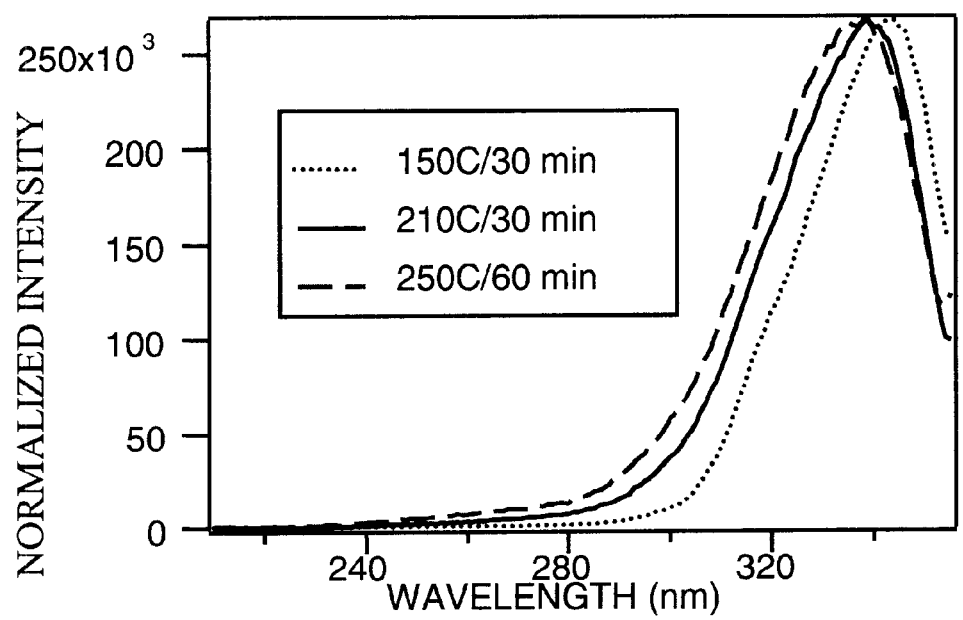
FIG. 9 is a graph normalized by forcing peak intensity to a maximum value showing peak emission versus excitation wavelength for CYCLOTENE™ BCB based resin at varying degrees of cure in nitrogen atmosphere.
Figure 10:
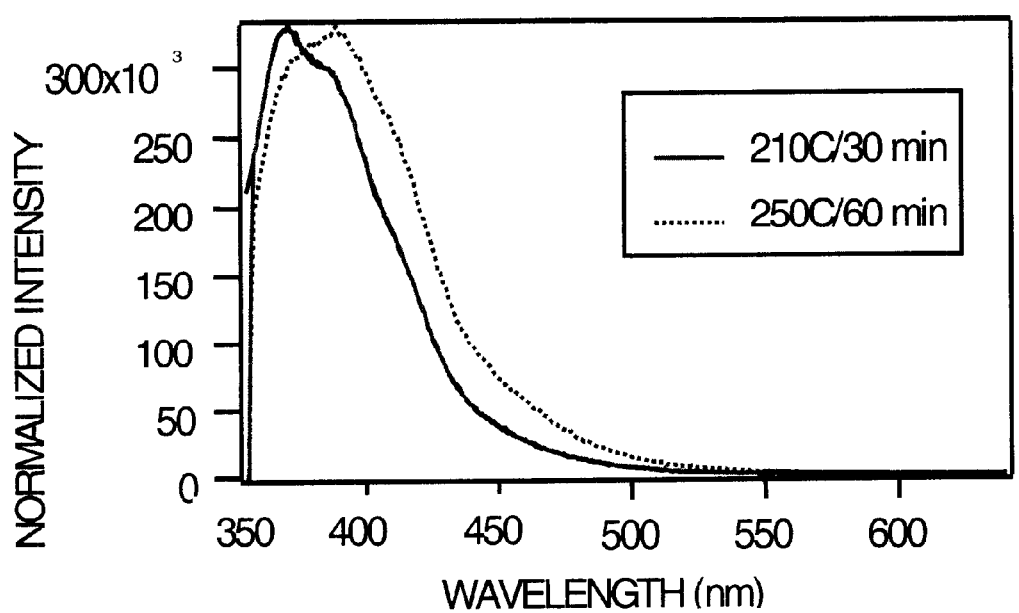
FIG. 10 is a graph normalized by forcing peak intensity to a maximum value showing emission spectra for CYCLOTENE BCB based resin at varying degrees of cure in a nitrogen atmosphere.

In FIGS. 9 and 10, the peak intensity was forced to the maximum value for plotting and comparison purposes. The spectra in FIG. 9 show that the peak in the excitation spectrum shifts to the blue with increasing cure. The peak moves from 344 nm after solvent removal to 337 nm for the 250° C./60 minutes standard hard cure. This shift in peak position is easier to detect than a change in the absolute value of the fluorescence emission, and is an advantage of using this method. Emission spectra with excitation at 335 nm, shown in FIG. 10, also showed differences, which can be used as an indicator of cure. With increasing cure, the band at 370 nm decreases, while the shoulder at 390 nm increases. This resulted in a shift of the emission maximum to longer wavelengths. The relative peak height (I370/I390) of the two bands (or emission maximum) can, therefore, be used as an indicator of cure.

Example 4

Fluorescence Measurements of CYCLOTENE BCB Based Resin Oxidation

Figure 11:
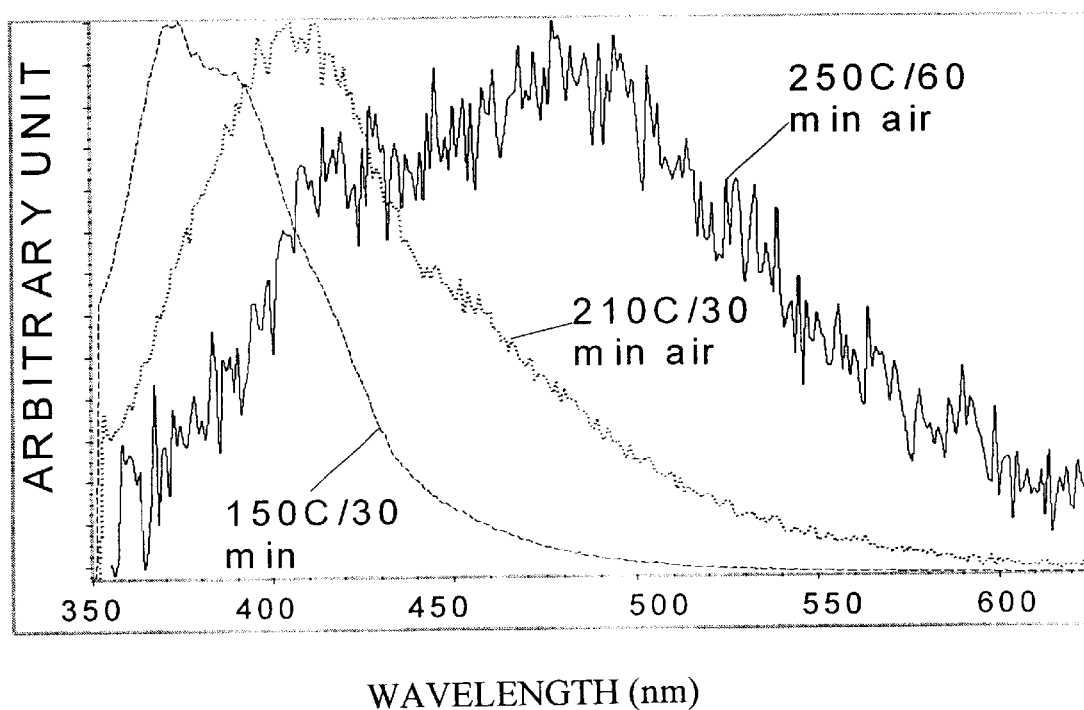
FIG. 11 is a graph normalized by forcing peak intensity to a maximum value showing emission spectra for CYCLOTENE BCB based resin at varying degrees of cure in air.

CYCLOTENE films were prepared as in Example 3, except that the 400° C. hot plate cures were done in air, not under nitrogen. The fluorescence emission spectra were collected as described in Example 3. As with FIGS. 9 and 10, in FIG. 11, the peak intensity was forced to the maximum value for plotting and comparison purposes. Since the magnitude of the curve for 60 minutes at 250° C. was very small, more noise was seen in this curve as it is forced to maximum for comparison purposes. The peak in the emission spectra, as shown in FIG. 11, was progressively shifted further to the red (i.e., higher wavelengths) with increased oxidation, from 371 nm to 475 nm. This was significantly larger than the shift in emission maximum with cure under nitrogen (371 to 389 nm in Example 3). Note also that the width of the emission band in FIG. 11 was affected by oxidation—the more oxidation, the broader the band. Therefore, monitoring the position of the emission maximum and/or band width can be used to determine the extent of oxidation of CYCLOTENE films in-situ.

Figure 12:
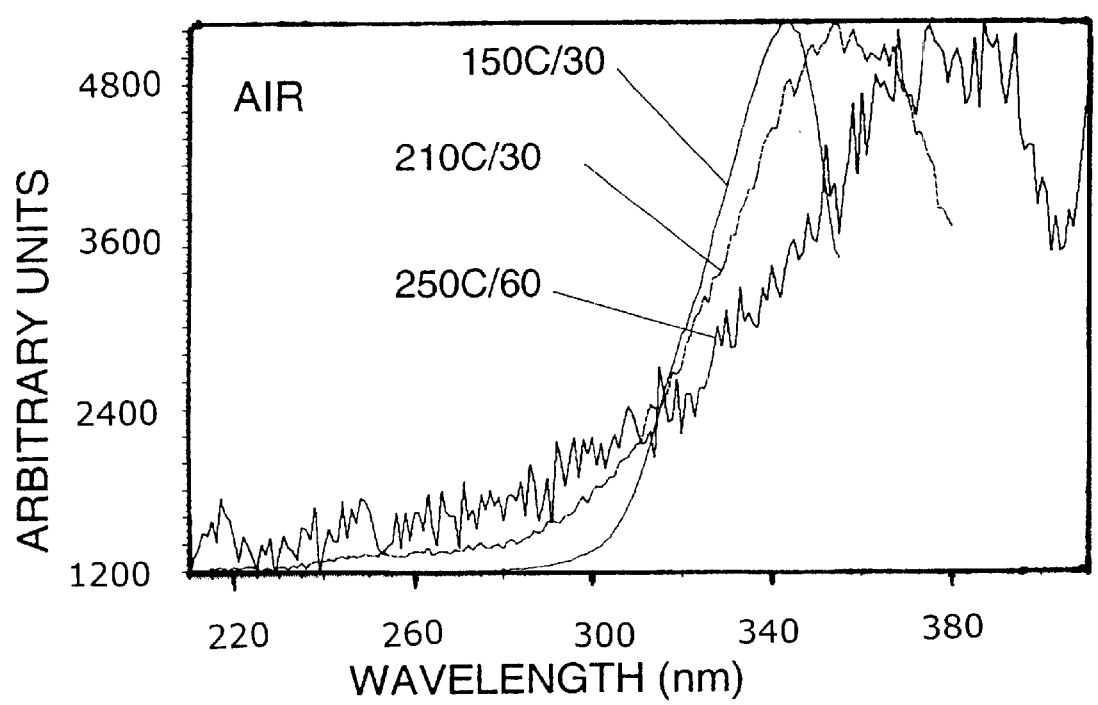
FIG. 12 is a graph normalized by forcing peak intensity to a maximum value showing peak emission versus excitation wavelength for CYCLOTENE BCB based resin at varying degrees of cure in air.

The fluorescence excitation spectra were also collected for these samples. As shown in FIG. 12, the excitation spectra shifts to the red (higher wavelengths) with increased oxidation. This shift was larger and in the opposite direction from the excitation maximum for cure in nitrogen. Again, however, band width can be another useful indicator to distinguish between cure and oxidation.

Example 5

Figure 13:
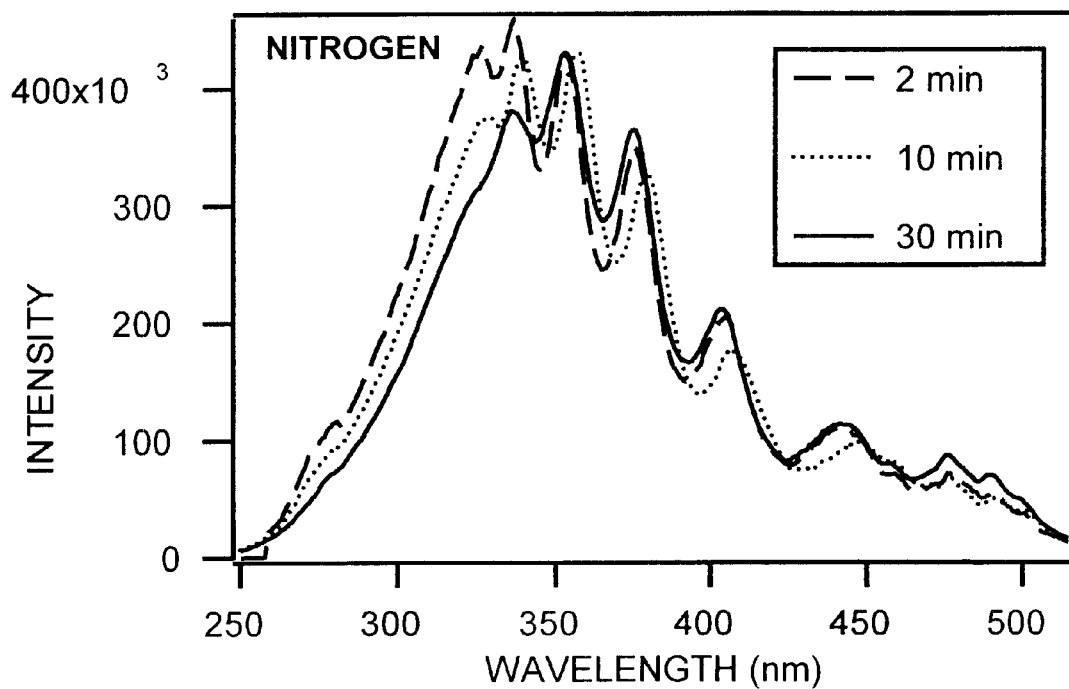
FIG. 13 is a graph of emission intensity versus excitation wavelength for the polymeric reaction product of a cyclopentadienone functional compound and an aromatic acetylene functional compound cured in a nitrogen atmosphere.
Figure 14:
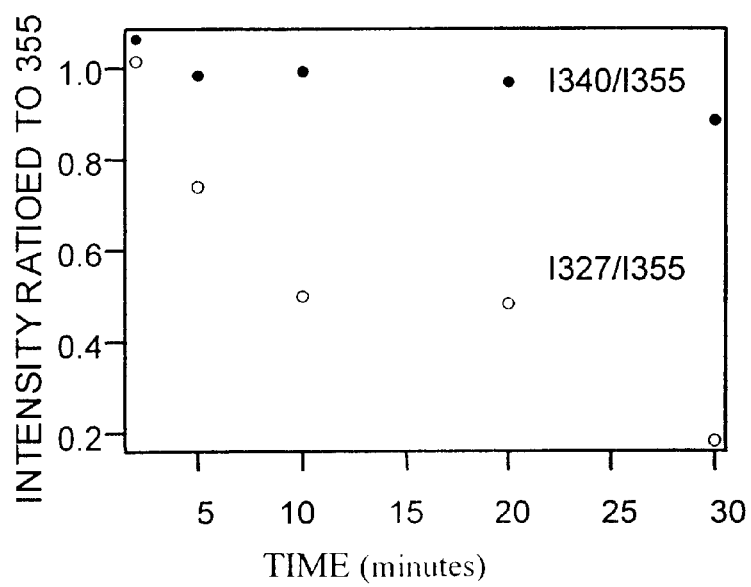
FIG. 14 is a graph of the normalized ratios of emission intensity at two emission wavelengths versus time of cure for the polymeric reaction product of a cyclopentadienone functional compound and an aromatic acetylene functional compound cured in a nitrogen atmosphere.

Fluorescence Excitation Measurements of the Reaction Product of A Biscyclopentadienone Compound and A Trifunctional Aromatic Acetylene Films were prepared as described in Example 1. Excitation spectra were collected on the samples using a Spex Fluorolog 1680 0.22 nm double spectrometer with front-face reflection optics, with emission collected at 536 nm. The excitation spectra were normalized by the intensity of the band near 355 nm. These spectra, shown in FIG. 13, reveal two bands change with cure time—one at 327 nm, the other at 340 nm. The plot of the normalized ratios I340/I355 and I337/I355 in FIG. 14 shows a decrease with cure time from 2 to 30 minutes, with a larger percentage change in the I327/I475 ratio. Both or either band can be used to quantitate cure.

Example 6

Fluorescence Excitation Spectra of Oxidation

Figure 15:
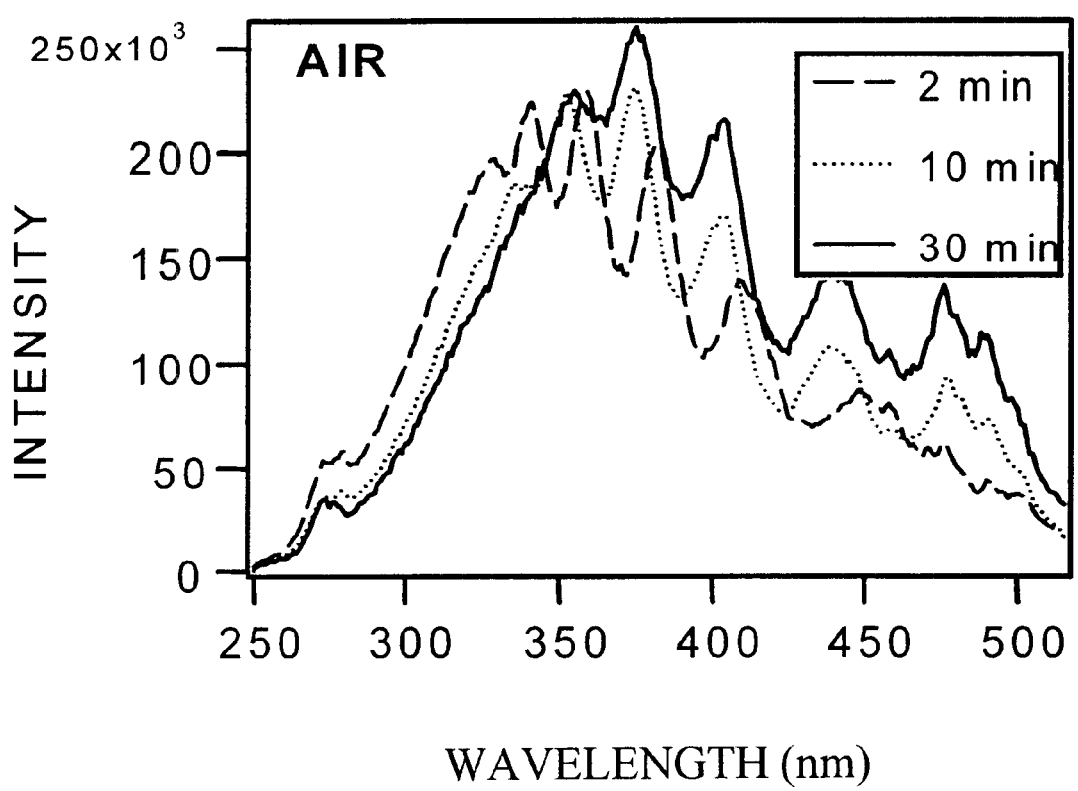
FIG. 15 is a graph of emission intensity versus excitation wavelength for the polymeric reaction product of a cyclopentadienone functional compound and an aromatic acetylene functional compound cured in air.

Films were prepared as in Example 5, except that the 400° C. hot plate cures were done in air, not under nitrogen. The excitation spectra were collected as in Example 5, and were likewise normalized by the intensity of the 355 nm band. The normalized excitation spectra of the films cured in air (see FIG. 15) showed a decrease in the intensity of bands near 327 and 340 nm, as was seen in the samples cured under nitrogen in Example 5, since the polymer was still curing to some extent even in the presence of oxygen. However, there was also a decrease with cure time in a band near 275 nm, and increases with cure time in the intensity of bands near 375, 400, 450 and 475 nm. The oxidation of these polymers, therefore, can be quantified by measuring the normalized ratios I375/I355, I400/I355, I450/I355 or I475/I355.

What is claimed is:

1. A method for simultaneous monitoring of the degree of cure and oxidation of an organic, spin-on dielectric material comprising the steps of preparing the sample by coating a thin film of a precursor material, which is free of fluorescent probe molecules onto a substrate and subjecting the precursor material to conditions to attempt to cause cure of the precursor to an organic, aromatic, polymer having a dielectric constant of less than 3.0, exposing the sample to radiation having a wavelength in the range of 200 to 500 nm, detecting a resulting emission of radiation, and comparing the emission to an emission for at least one standard for the polymer, which standard has a known degree of cure and a known degree of oxidation, thereby obtaining an estimated degree of cure and estimated degree of oxidation for the sample.

2. The method of claim 1 wherein the polymer is a polyarylene.

3. The method of claim 1 wherein the polymer is the reaction product of a cyclopentadienone functional compound and an aromatic acetylene functional compound.

4. The method of claim 1 wherein the detecting and comparing steps comprise measuring emission intensity at emission wavelengths corresponding to a cure responsive wavelength, an oxidation responsive wavelength, and a wavelength not responsive to either cure or oxidation; normalizing by dividing each of the emission intensities at the cure responsive wavelength and the oxidation responsive wavelength by the emission intensity at the non-responsive wavelength to obtain a cure intensity ratio and an oxidation intensity ratio; and comparing the cure intensity ratio and the oxidation intensity ratio to a cure intensity ratio and an oxidation intensity ratio for at least one standard having a known degree of cure and oxidation.

5. The method of claim 1 further comprising adjusting cure conditions based on the estimated degree of cure and the estimated degree of oxidation.

6. The method of claim 5 wherein the cure condition, which is adjusted, is selected from temperature, time, ambient environment, or a combination thereof.

7. The method of claim 1 wherein the comparing step comprises comparing either the peak excitation wavelength or the peak emission wavelength of the sample to a peak excitation wavelength or peak emission wavelength of at least one standard having a known degree of cure and oxidation.

8. The method of claim 4 wherein the polymer is the reaction product of a cyclopentadienone functional compound and an acetylene functional compound.

9. The method of claim 8 wherein the cure responsive wavelength is in the range of about 380 to 440 nm, the oxidation responsive wavelength is in the range of 500 to 650 nm, and the non-responsive wavelength is preferably in the range of 460 to 500 nm.

10. The method of claim 8 wherein the cure responsive wavelength is in the range of 390 to 400 nm or 420 to 430 mn, the oxidation responsive wavelength is in the range of 520 to 550 nm, and the non-responsive wavelength is preferably in the range of 470 to 480 nm.

11. The method of claim 1 wherein the substrate comprises a silicon wafer.

12. The method of claim 1 wherein the polymer is a benzocyclobutene based resin.

13. The method of claim 1 wherein the comparing step comprises comparing, on a plot of emission intensity versus either excitation wavelength or emission wavelength, a width of peak emission intensity at half the height of the peak to a width of peak emission intensity at half the height of the peak for a standard having a known degree of cure and oxidation.

* * * * *